United States Patent [19]
Youngdale

[11] 4,067,891
[45] Jan. 10, 1978

[54] 2A,2B-DIHOMO-16,16-DIMETHYL-PGF$_2$ANALOGS

[75] Inventor: Gilbert A. Youngdale, Portage, Mich.

[73] Assignee: The Upjohn Company, Kalamazoo, Mich.

[21] Appl. No.: 726,447

[22] Filed: Sept. 24, 1976

Related U.S. Application Data

[63] Continuation of Ser. No. 550,368, Feb. 18, 1975, abandoned.

[51] Int. Cl.$^2$ .......................................... C07C 177/00
[52] U.S. Cl. ........................... 260/410.9 R; 260/404; 260/404.5; 260/410.5; 260/413; 424/305; 424/318; 542/426

[58] Field of Search ....... 260/468 D, 514 D, 410.9 R, 260/413

[56] References Cited

U.S. PATENT DOCUMENTS 3,892,795   1/1975   Magerlin ...................... 260/468

Primary Examiner—Robert Gerstl
Attorney, Agent, or Firm—Robert A. Armitage

[57] ABSTRACT 2a,2b-Dihomo-16,16-dimethyl-PGF- and PGE-type compounds are disclosed with processes for making them. These compounds are useful for a variety of pharmacological purposes, including anti-ulcer, inhibition of platelet aggregation, increase of nasal patency, reproductive cycle control, and wound healing.

7 Claims, No Drawings

2A,2B-DIHOMO-16,16-DIMETHYL-PGF₂ ANALOGS

This is a continuation of application Ser. No. 550,368, filed Feb. 18, 1975, now abandoned.

BACKGROUND OF THE INVENTION

This invention relates to novel compositions of matter, to novel methods for producing them, and to novel chemical intermediates useful in those processes. Particularly, this invention relates to certain novel analogs of prostaglandins $E_1$, $F_{1\alpha}$, $F_{1\beta}$, $E_2$, $F_{2\alpha}$, and $F_{2\beta}$ in which the carboxy-terminated chain contains an additional ethylene group and the hydrogens attached at the C-16 position in the prostanoic acid structure are replaced by methyl groups.

The known prostaglandins include, for example, prostaglandin $E_1$ (PGE₁), prostaglandin $F_1$ alpha and beta (PGF$_{1\alpha}$ and PGF$_{1\beta}$), prostaglandin $E_2$ (PGE₂), and prostaglandin $F_2$ alpha and beta (PGF$_{2\alpha}$ and PGF$_{2\beta}$). Each of the above-mentioned known prostaglandins is a derivative of prostanoic acid which has the following structure and atom numbering:

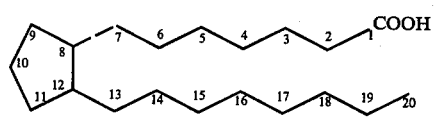   I

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE₁ has the following structure:

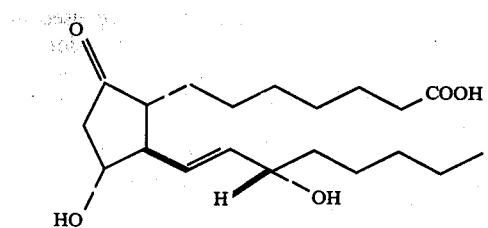   II

PGF$_{1\alpha}$ has the following structure:

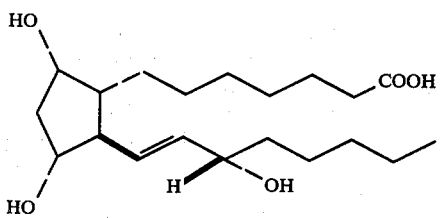   III

PGF$_{1\beta}$ has the following structure:

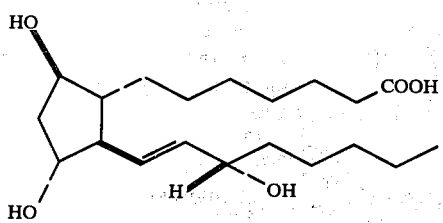   IV

PGE₂ has the following structure:

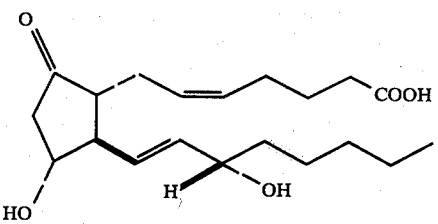   V

PGF$_{2\alpha}$ has the following structure:

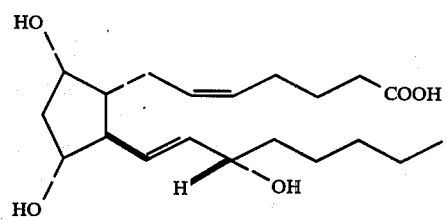   VI

PGF$_{2\beta}$ has the following structure:

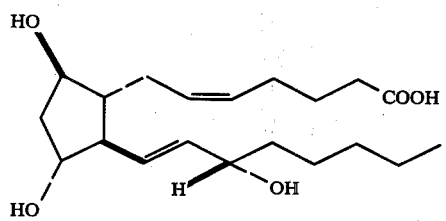   VII

In formulas II to VII, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to VII is in S configuration. See Nature, 212, 38 (1966) for discussion of the stereochemistry of the prostaglandins.

The expressions "C-15" and the like identify the carbon atom in the prostaglandin or prostaglandin analog which is in the position corresponding to the position of the carbon atom of the same number in prostanoic acid (See formula I).

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin. For convenience hereinafter, use of the terms, PGE₁, PGF$_{1\alpha}$, PGF$_{1\beta}$, and the like, will mean the optically active form of that prostaglandin with the same absolute configuration as PGE₁ obtained from mammalian tissues.

PGE₁, PGE₂, and the corresponding PGF$_\alpha$, and PGF$_\beta$ compounds, and their esters, and pharmacologically acceptable salts, are estremely potent in causing various biological responses. For that reason, these compounds are useful for pharmacological purposes. See, for example, Bergstrom et al., Pharmacol. Rev. 20, 1 (1968), and references cited therein. A few of those biological responses are; antilipolytic activity as shown by antagonism of epinephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application. The exact dose depends upon the age, weight, and condition of the patient and on the frequency and route of administration.

The PGE, $PGF_\alpha$, and $PGF_\beta$ compounds are useful in the treatment of asthma. For example, these compounds are useful as bronchodilators or as inhibitors of mediators, such as SRS-A and histamine, which are released from cells activated by an antigen-antibody complex. Thus these compounds control spasm and facilitate breathing in conditions such as bronchial asthma, bronchitis, bronchiectasis, pneumonia, and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact does depending on the age, weight, and condition of the patient and on the frequency and route of administration. For the above use these prostaglandins can be combined advantageously with other antiasthmatic agents, such as sympathomimetics (isoproterenol, phenylephrine, ephedrine, etc.); xanthine derivatives (theophylline and aminophylline); and corticosteroids (ACTH and prednisolone). Regarding use of these compounds see South African Pat. No. 681,055.

The PGE compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF_\alpha$, and $PGF_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGF$_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the normal mammalian gestation period, especially the first and second trimesters.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically. PGE$_2$, for example, is administered orally or vaginally at doses of about 5 to 50 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptomatic alleviation, and cure of diseases involving abnormal lipid mobilization and high free fatty acid levels, e.g., diabetes mellitus vascular diseases, and hyperthyroidism.

The PGE compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts especially small, deep (Davis) grafts which are intended to cover skinless areas by subsequent outward growth rather than initially, and to retard rejection of homografts.

For these purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 2000 $\mu$g./ml. of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.)

The PGF$_\alpha$, PGF$_\beta$, and PGE compounds are also useful in reducing the undesirable gastrointestinal effects resulting from systemic administration of anti-inflammators prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$ and PGE$_2$. Prostaglandin compounds are useful, for example, in reducing the undesirable gastrointestinal effects resulting from systemic administration of indomethacin, phenylbutazone, and aspirin. These are substances specifically mentioned in Partridge et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

Several related compounds have been reported in the literature. 2a,2b-Dihomo-PGE$_1$ and 2a,2b-dihomo-PGE$_2$ have been reported by Struijk, et al., Nobel Symposium 2:51 (1967).

SUMMARY OF THE INVENTION

This invention provides novel 2a,2b-dihomo-16,16-dimethyl prostaglandin E$_1$, E$_2$, F$_{1\alpha}$, F$_{2\alpha}$, F$_{1\beta}$, and F$_{2\beta}$analogs. Further, it provides both epimeric configurations at C-15 and provides esters and pharmacologically acceptable salts of said analogs. It also provides novel processes for preparing the hereinabove described analogs, esters, and salts.

The novel prostaglandin analogs of this invention each have an ethylene group inserted between C-2 and C-3 in the carboxy terminated chain. Also at the C-16 position the novel prostaglandin analogs have two methyl groups in place of the hydrogen attached to C-16. Also both epimeric configurations at C-15 are provided. These compounds are represented by the generic formula

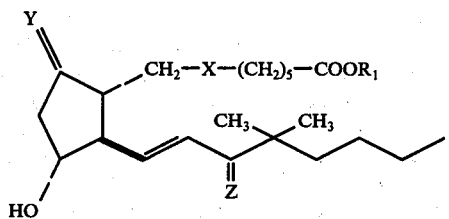

wherein X is cis—CH=CH— or —CH$_2$CH$_2$—; wherein Y is =O,

or

wherein Z is

or

wherein R$_1$ is hydrogen, alkyl of one to 12 carbon atoms, inclusive, a pharmacologically acceptable cation,

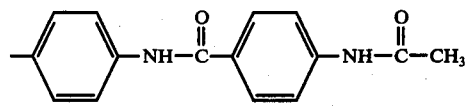

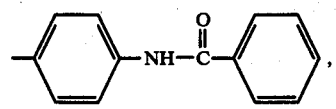

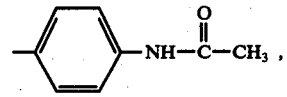

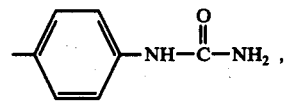

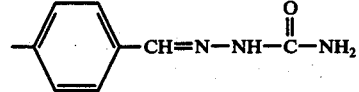

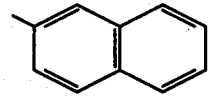

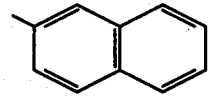

Examples of the alkyl esters of one to 12 carbon atoms included in this invention are methyl, ethyl, propyl, butyl, pentyl, hexyl, heptyl, octyl, nonyl, decyl, undecyl, dodecyl, and isomeric forms thereof.

Included in the novel compounds of this invention are the 15-epimers. Where the hydroxy group configuration at C-15 is the same as that of the natural prostaglandin PGE$_1$, identified as the "R" configuration in the prostaglandin analogs of this invention and the "S" configuration for the prostaglandins, no stereochemical designation is provided. When the 15-epimer is intended the name of the analog will include "15-epi". When both epimeric forms are intended the name of the prostaglandin analog will include "15(RS)". Further since the carboxy-terminated side chain of the novel compounds of this invention have an ethylene group inserted between C-2 and C-3, the names of the novel compounds of this invention include "2a,2b-dihomo".

The numerical designation of the skeletal carbon atoms is unchanged, except that between C-2 and C-3 will be carbon atoms numbered as C-2a and C-2b. Also, since two methyl groups replace the hydrogens at C-16, the name of the novel compounds of this invention include "16,16-dimethyl".

For example, 2a,2b-dihomo-16,16-methyl-PGE₁ one of the novel compounds of this invention, is represented by:

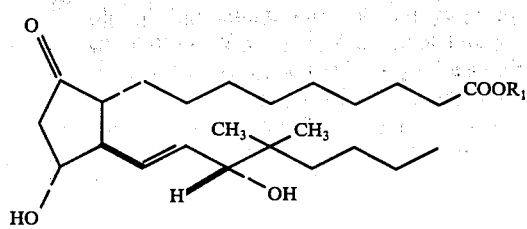

VIII when R₁ is hydrogen.

A 15-epimer of Formula VIII, 2a,2b-dihomo-15-epi-16,16-di-methyl-PGE₁ is also a novel compound of this invention and is represented by:

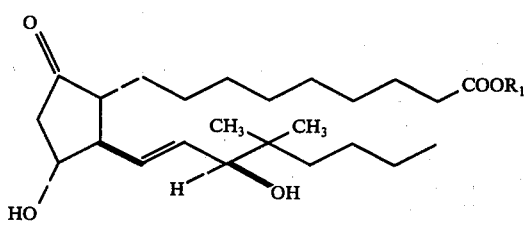

IX wherein R₁ is hydrogen.

2a,2b-Dihomo-16,16-dimethyl-PGE₂, another compound of this invention, is represented by:

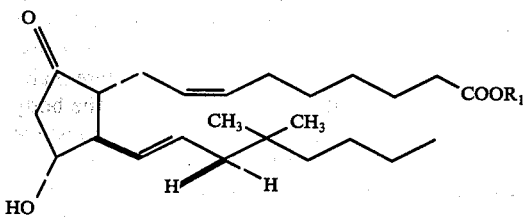

X when R₁ is hydrogen.

2a,2b-Dihomo-15-epi-16,16-dimethyl-PGE₂, another compound of this invention, is represented by:

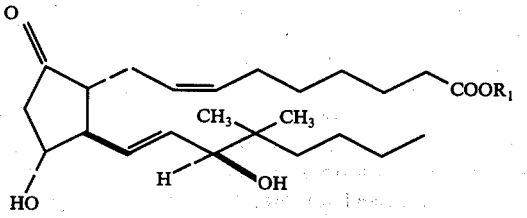

XI when R₁ is hydrogen.

The PGF$_\alpha$- and PGF$_\beta$-type compounds of this invention can be similarly represented. For example, 2a,2b-dihomo-16,16-dimethyl-PGF$_{1\alpha}$ and 2a,2b-dihomo-16,16-dimethyl-PGF$_{1\beta}$ are represented by:

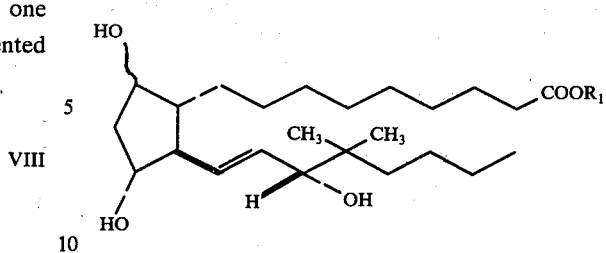

XII when ~ indicates attachment of the hydroxyl group to the cyclopentane ring in the alpha or beta configuration, i.e., ~ is alpha or beta, respectively, and R₁ is hydrogen.

Also included in the invention, for example, are the 15-epi compounds, 2a,2b-dihomo-15-epi-16,16-dimethyl-PGF$_{1\alpha}$, and 2a,2b-dihomo-15-epi-16,16-dimethyl-PGF$_{1\beta}$, which can be represented by:

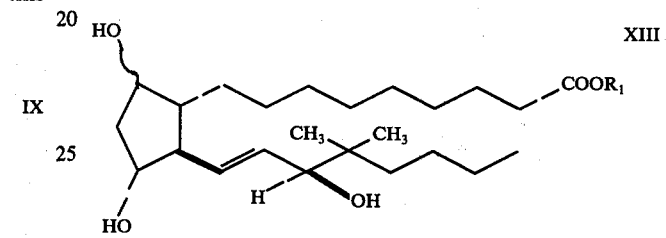

XIII when ~ indicates either alpha or beta attachment and R₁ is hydrogen.

The 15(S) and 15(R) compounds of the PGF₂ series, 2a,2b-dihomo-16,16-dimethyl-PGF$_{2\alpha}$, 2a,2b-dihomo-16,16-dimethyl-PGF$_{2\beta}$, 2a,2b-dihomo-15-epi-16,16-dimethyl-PGF$_{2\alpha}$, and 2a,2b-dihomo-15-epi-16,16-dimethyl-PGF$_{2\beta}$, can be represented by:

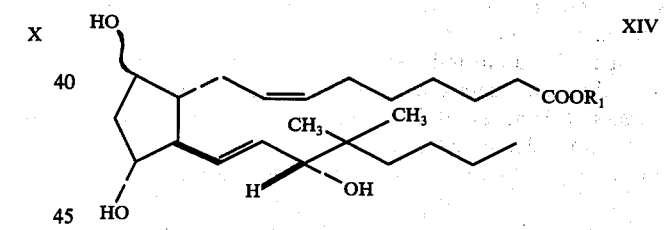

XIV when ~ is alpha or beta, and R₁ is hydrogen, and by:

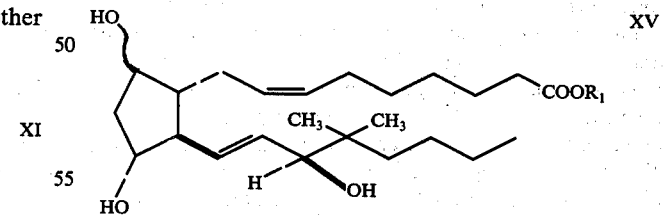

XV when ~ is alpha or beta, and R₁ is hydrogen.

To obtain the optimum combination of biological response, specificity, potency, and duration of activity, certain compounds within the scope of formulas VIII to XV are preferred. With reference to the definitions given above it is preferred that R₁ when an alkyl ester by either methyl or ethyl for optimum absorption of the compound by the experimental animal system. It is especially preferred for this purpose that R₁ be methyl. If a prolonged duration of activity is desired, it is especially preferred that if R₁ is alkyl, it be straight chained octyl, nonyl, decyl, undecyl, or dodecyl. When $R_1$ is not alkyl it is preferred that $R_1$ be hydrogen,

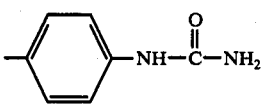

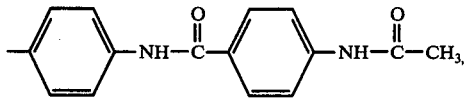

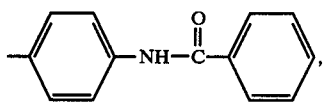

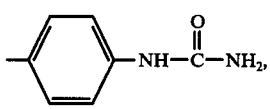

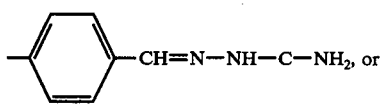

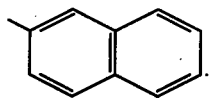

The 15(R) configuration is also preferred.

Pharmacologically acceptable salts of these formula VIII to XV compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel formula VIII to XV compounds of this invention each cause the biological responses described above for the PGE, $PGF_\alpha$, and $PGF_\beta$, compounds, respectively, and each of these novel compounds is accordingly useful for the above-described corresponding purposes, and is used for those purposes in the same manner as described above.

The known PGE, $PGF_\alpha$, and $PGF_\beta$ compounds are all potent in causing multiple biological responses even at low doses. Moreover, for many applications, these known prostaglandins have an inconveniently short duration of biological activity. Therefore, each of these novel prostaglandin analogs is surprisingly and unexpectedly more useful than one of corresponding abovementioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Another advantage of the novel compounds of this invention, especially the preferred compounds defined hereinabove, compared with the known prostaglandins is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

As discussed above, the compounds of formulas VIII to XV are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula VIII to XV compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers, are used for oral sublingual administration. For rectal or vaginal administration, suppositories prepared as known in the art are used. For tissue implants, a sterile tablet or silicone rubber capsule or other object containing or impregnated with the substance is used.

The prostaglandin analogs encompassed by formulas VIII through XV are produced by the reactions and procedures described and exemplified hereinafter.

Reference to Chart A herein will make clear the processes which yield the 2a,2b-dihomo-16,16-dimethyl PGF-type and PGE-type compounds of this invention.

In the Chart, $R_1$, $R_2$, and X are as hereinabove defined; $R_3$ is an acyl protecting group. Acyl protecting which are useful for the purposes described hereinbelow include:

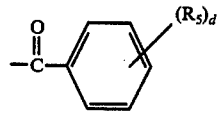 (1)

wherein $R_5$ is alkyl of one to 4 carbon atoms, inclusive, phenylalykl of 7 to 10 carbon atoms, inclusive, or nitro, and $d$ is zero to 5, inclusive, provided that not more than two $R_5$'s are other than alkyl, and that the total number of carbon atoms in the $R_5$'s does not exceed 10 carbon atoms;

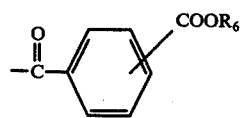 (2)

wherein $R_6$ is alkyl of one to 4 carbon atoms, inclusive;
(3)

CHART A

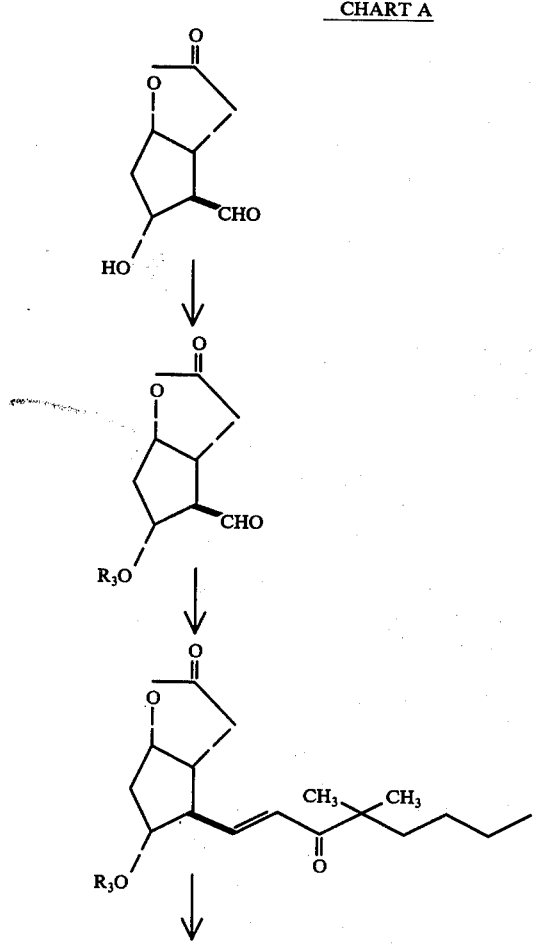

CHART A -continued

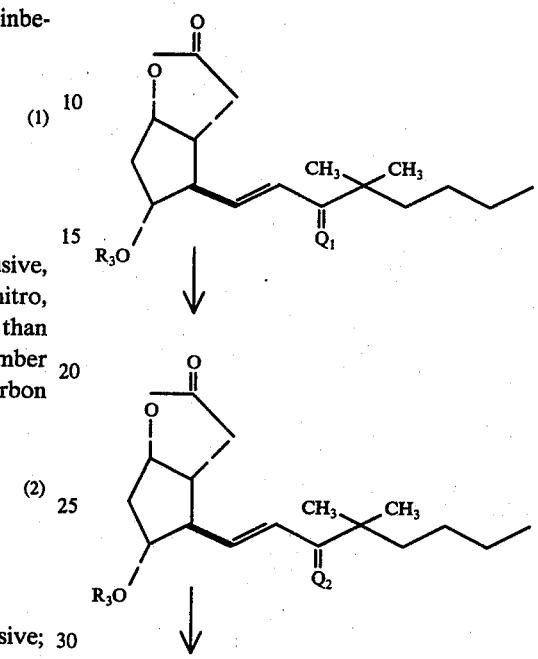

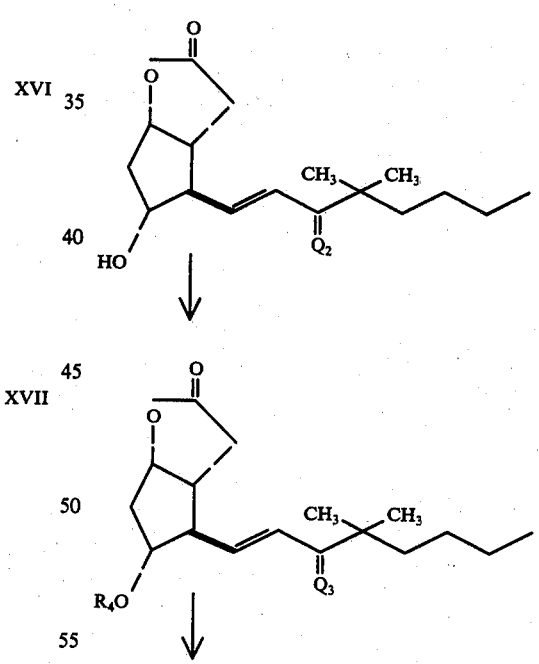

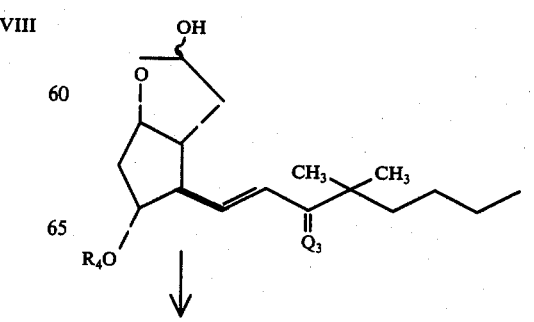

-continued
CHART A

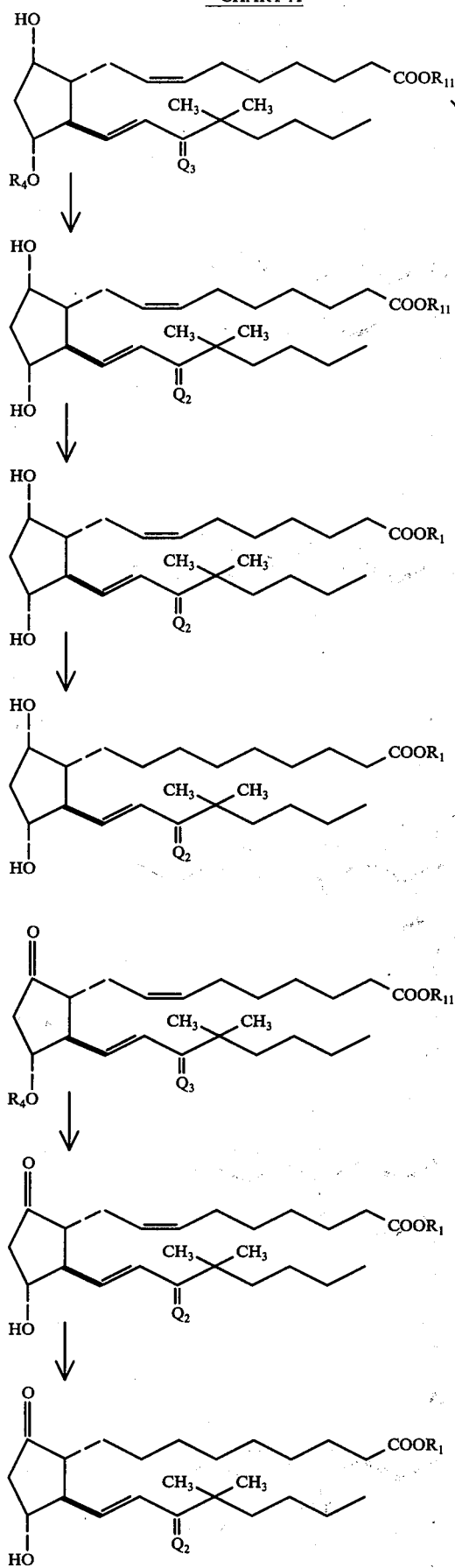

-continued
CHART A

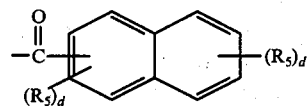

wherein $R_5$ and $d$ are as defined above and may be the same or different for each ring; or (4) acetyl. (Use of acetyl or p-phenylbenzoyl is known in the art. See Corey et al., J. Am. Chem. Soc. 93, 1491 (1971)).

$R_3$ is for example, benzoyl; substituted benzoyl, e.g. (2-, 3-, or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, (2-, 3-, or 4-)phenethylbenzoyl, (2-, 3-, or 4-)nitrobenzoyl, (2,4-; 2,5-; or 3,5-)-dinitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

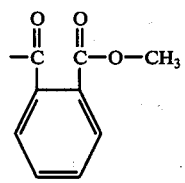

isophthaloyl, e.g.

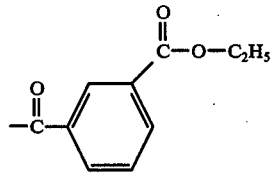

or

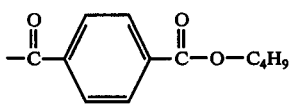

(1- or 2-)naphthoyl; and substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl and (5- or 8-)nitro-2-naphthoyl.

Likewise $R_4$ is hydrogen or a blocking group, which is defined as any group which replaces hydrogen of the hydroxy groups, which is not attacked by nor is reactive to the reagents used in the respective transformations to the extent that the hydroxy group is, and which is subsequently replaceable by hydrogen at a later stage in the preparation of the prostaglandin-like products. Several blocking groups are known in the art, e.g. tetrahydropyanyl and substituted tetrahydropyranyl (see Corey, Proceedings of the Robert A. Welch Foundation Conferences on Chemical Research XII, Organic Synthesis, pp. 51–79 (1969)). Those blocking groups which have been found useful include:
1. tetrahydropyranyl;
2. tetrahydrofuranyl;
3. a group of the formula

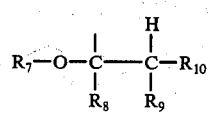

wherein R$_7$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R$_8$ and R$_9$ are the same of different, being hydrogen, alkyl of one to 4 carbon atoms, inclusive, phenyl or phenyl substituted with one, 2, or 3 alkyl of one to 4 carbon atoms, inclusive, or, when R$_8$ and R$_9$ are taken together, —(CH$_2$)$_a$— or —(CH$_2$)$_b$—O—(CH$_3$)$_c$— wherein $a$ is 3, 4, or 5, $b$ is one, 2, or 3, and $c$ is one, 2, or 3 with the proviso that $b$ plus $c$ is 2, 3, or 4, and wherein R$_{10}$ is hydrogen or phenyl;

4. a silyl group of the formula —Si(G)$_3$ wherein G is alkyl of one to 4 carbon atoms, inclusive, aralkyl of 7 to 12 carbon atoms, inclusive, phenyl or phenyl substituted with one or 2 fluoro, chloro, or alkyl of one to 4 carbon atoms, inclusive, and wherein the various G's of a —Si(G)$_3$ moiety are alike or different, or 5. a group of the formula

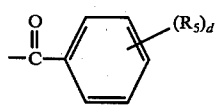

wherein $d$ and R$_5$ are defined hereinabove. R$_{11}$ is hydrogen or alkyl of one to 12 carbon atoms, inclusive. R$_{12}$ is R$_{11}$ or a pharmacologically acceptable cation.

Further in these charts Q$_1$ is a mixture of

and

Q$_2$ is either

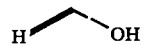

or

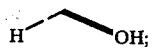

Q$_3$ is either

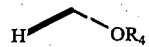

or

wherein R$_4$ is as defined hereinabove, and ∼ indicates attachment of hydroxyl to the ring in alpha or beta configuration.

The procedure steps of Chart A are known in the art. For process steps XVI to XXI see German Offenlegungsschrift 2,217,004, Derwent Farmdoc No. 71483T-B. Further the formula-XVI or XVII starting material is known in the art or prepared by methods known in the art.

The formula-XXII compound is obtained from the formula-XXI compound by replacement of the hydrogen atoms of the hydroxy groups of the formula XXI compound with the blocking groups of the formula R$_4$. When the blocking group is tetrahydropyranyl or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess preferably at 1.0 to 1.2 times the stoichiometric amount. The reaction is carried out at about 20° to 50° C. When the blocking is of the formula Si-(G)$_3$, silylation procedures known in the art are used. See, for example, Pierce, Silylation of Organic Compounds, Pierce Chemical Co. (1968).

When the blocking group is of the formula

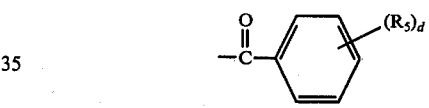

wherein R$_5$ and $d$ are as defined above, procedures known in the art are used such as in U.S. Pat. No. 3,778,450, for the acylation of compounds. Where the blocking group is of the formula

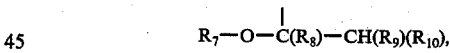

wherein R$_7$, R$_8$, R$_9$, and R$_{10}$ are as defined above, the appropriate reagent is a vinyl ether e.g. isobutyl vinyl ether or any vinyl ether of the formula R$_7$—O—C(R$_8$)=C(R$_9$)—(R$_{10}$), wherein R$_7$, R$_8$, R$_9$, and R$_{10}$ are defined above; or an unsaturated cyclic or heterocyclic compound, e.g. 1-cyclo-hexen-1-yl or 5,6-dihydro-4-methoxy-2H-pyran. See C. B. Reese et al., Journal of American Chemical Society 89, 3366 (1967). The reaction conditions for such vinyl ethers and unsaturates are similar to those for dihydropyran above.

The formula-XXIII lactol is obtained on reduction of the formula-XXII lactone without reducing the ethylenic group. For this purpose, diisobutyl aluminum hydride is used as known in the art. The reduction is preferably done at −70 ° to −80° C.

The formula-XXIV compound is obtained by a Wittig alkylation of the lactol, the formula-XXIII compound, using the methods known in the art. When R$_{11}$ is hydrogen the phosphonium salt used in the Wittig reaction is a (6-carboxyhexyl)triphenylphosphonium halide, preferably bromide. When R$_{11}$ is an alkyl ester the corresponding [6-(alkoxycarbonyl)hexyl]triphenylphosphonium halide, preferably bromide, is used. For optimum yield it is preferred that the Wittig reaction be performed so as to yield the free acid. Thus, by this preferred route the (6-carboxyhexyl)triphenylphosphonium halide is used.

The formula-XXV compound is then obtained from the formula-XXIV compound by hydrolysis of the blocking groups. Useful reagents for this purpose are hydrochloric acid in methanol, a mixture of acetic acid, water, and tetrahydrofuran, aqueous citric acid, or aqueous phosphoric acid in tetrahydrofuran, perferably at temperatures below 55° C., thereby avoiding undesirable side reactions.

The formula-XXVI compound is then prepared from the formula-XXV compound by transformation of the $R_{11}$ moiety to an $R_1$ moiety using the procedures and methods hereinbelow described.

The formula-XXVII compound is then prepared from the formula-XXVI compound by catalytic hydrogenation of the 5,6-cis double bond. For example, using one atmosphere of hydrogen and a palladium-on-charcoal catalyst at −15° C. the formula-XXXVII compound is prepared. See for reference B. Samuelsson, Journal of Biological Chemistry, 239 491 (1964).

The formula-XXVIII compound is also prepared from the formula-XXIV compound. In the preparation of the formula-XXVIII compound, the formula-XXIV compound is oxidized at the C-9 hydroxy position. This oxidation is carried out by methods known in the art, preferably by use of the Jones reagent or the Collins reagent.

The formula-XXIX compound is then prepared from the formula-XXVIII compound by hydrolysis of the blocking groups as is described above for the preparation of the formula-XXV compound from the formula-XXIV compound.

The formula-XXX compound is prepared from the formula-XXXIX compound by catalytic hydrogenation of the cis-5,6-double bond. Methods as described above for catalytic hydrogenation of the formula-XXVI compound are employed.

Chart B provides a methods whereby the PGE-type compounds of this invention are transformed to corresponding PGF-type compounds.

With respect to Chart B the formula-XXXII compound is prepared from the formula-XXXI compound by a ring carbonyl reduction. These ring carbonyl reductions are carried out by methods known in the art. See, for example, Bergstrom

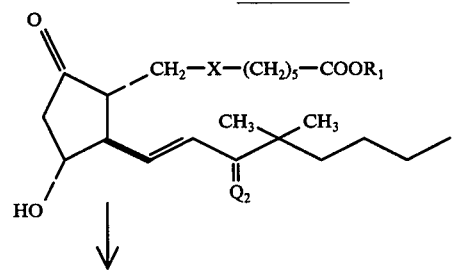

CHART B

XXXI

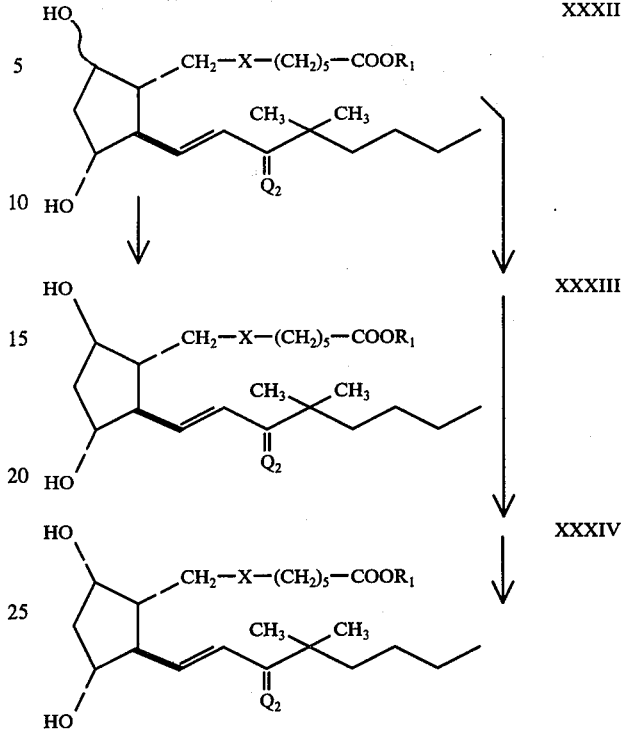

et al., Arkiv Kemi, 19, 563 (1963), Acta. Chem. Scand. 16, 969 (1962), and British Specification No. 1,097,533. Any reducing agent is used which does not react with carbon-carbon double bonds or ester groups. Preferred reagents are lithium (tri-tert butoxy) aluminum hydride, the metal borohydrides, especially sodium, potassium, and zinc borohydrides, the metal trialkoxy borohydrides, e.g. sodium trimethoxy borohydride.

The formula-XXXIII and formula-XXXIV compounds are prepared by separating the C-9 hydroxy epimeric mixtures into the individual alpha and beta epimers. Methods known in the art for separation of analogous pairs of known epimeric prostanoic acid derivatives are employed. See, for example, Bergstrom et al., cited above, Granstrom et al., Journal of Biological Chemistry 240, 457 (1965) and Green et al., Journal of Lipid Research, 5, 117 (1964). Known to be useful as separation methods are partition chromatographic procedures, both normal and reversed phase, preparative thin layer chromatography, and counter current distribution procedures.

As discussed above, the processes herein described lead variously to acids ($R_1$ is hydrogen) or to esters.

When the alkyl ester has been obtained and an acid is desired, saponification procedures, as known in the art for F-type prostaglandins may be used.

For alkyl esters of E-type prostaglandins enzymatic processes for transformation of esters to their acid forms may be used by methods known in the art. See for reference E. G. Daniels, Producing an Esterase, U.S. Pat. No. 3,761,356.

When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, 1-diazo-2-ethylhexane, and diazodecane, for example, gives the ethyl, butyl, 2-ethylhexyl, and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing the following esters of this invention:

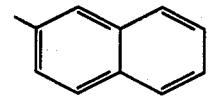

-continued from corresponding phenols or naphthol and the free acid PG compounds differing as to yield and purity of product.

Thus by one method, the PG compound is converted to a tertiary amine salt, reacted with pivaloyl halide to give the mixed acid anhydride and then reacted with the phenol. Alternatively, instead of pivaloyl halide, an alkyl or phenylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231-236, John Wiley and Sons, Inc., New York (1967). The PG compound is contacted with one to ten molar equivalents of the phenol in the presence of 2-10 molar equivalents of dicyclohexylcarbodiimide in pyridine as a solvent.

The preferred novel process for the preparation of these esters, however, comprises the steps (1) forming a mixed anhydride with the PG compound and isobutylchloroformate in the presence of a tertiary amine and (2) reacting the anhydride with an appropriate phenol or naphthol.

The mixed anhydride is represented by the formula.

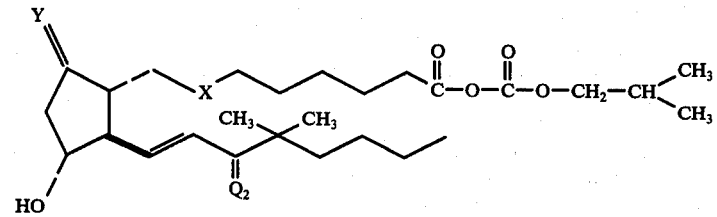

for the optically active PG compounds, wherein $Q_2$, X, and Y have the same definition as above.

The anhydride is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the PG compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The phenol is preferably used in equivalent amounts or in excess to insure that all of the mixed anhydride is converted to ester. Excess phenol is separated from the product by methods described herein or known in the art, for example by crystallization. The tertiary amine is not only a basic catalyst for the esterification but also a convenient solvent. Other examples of tertiary amines useful for this purpose include N-methylmorphine, triethylamine, diisopropylethylamine, and dimethylaniline. Although they may be used, 2-methyl-pyridine and quinoline result in a slow reaction. A highly hindered

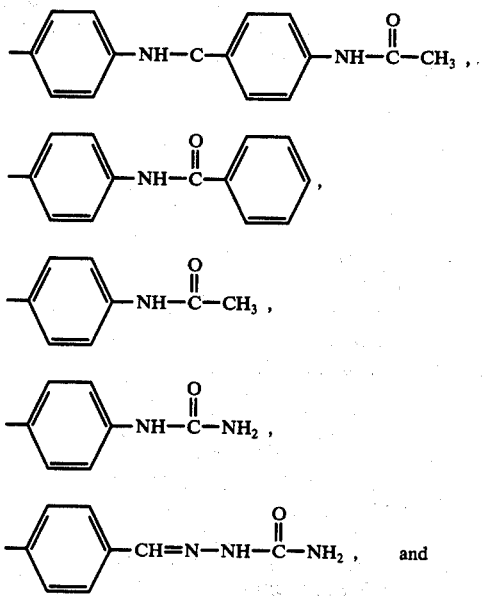

amine such as 2,6-dimethyl-pyridine is not useful because of the slowness of the reaction.

The reaction with the anhydride proceeds smoothly at room temperature (about 20° to 30° C.) and can be followed in the conventional manner with thin layer chromatography.

The reaction mixture is worked up to yield the ester following methods known in the art, and the product is purified, for example by silica gel chromatography.

Solid esters are converted to a free-flowing crystalline form on crystallization from a variety of solvents, including ethyl ecetate, tetrahydrofuran, methanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanoate, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition C a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of the PG-type free-hydroxy compound with a carboxyacylating agent, preferably the anhydride of a lower alkanoic acid, i.e., an alkanoic acid of two to 8 carbon atoms, inclusive. For example, use of actic anhydride gives the corresponding acetate. Similar use of propionic anhydride, isobutyric anhydride, and hexanoic acid anhydride gives the corresponding carboxyacylates.

EXAMPLES

The invention can be more fully understood by the following examples and preparations:

All temperatures are in degrees centigrade.

Infrared absorption spectra (IR) are recorded on a Perkin-Elmer Model 421 infrared spectrophotometer. Except when specified otherwise, undiluted (neat) samples are used.

Ultraviolet spectra (UV) are recorded on a Cary Model 15 spectrophotometer.

Nuclear Magnetic Resonance (NMR) spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

The collection of chromatographic eluate fractions starts when the eluant front reaches the bottom of the column.

"Brine", herein, refers to an aqueous saturated sodium chloride solution.

The A-IX solvent system used in thin layer chromatography (TLC) is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" (SSB) refers to mixed isomeric hexanes.

EtOAc refers to ethyl acetate.

Silica gel chromatography, as used herein, is understood to include elution, collection of fractions, and combination of those fractions shown by TLC (thin layer chromatography) to contain the desired product free of starting material and impurities.

Preparation 1

3α, 5α-Dihydroxy-2β-(3α-hydroxy-4,4-dimethyl-trans-1-octenyl)-1α-cyclopentane acetaldehyde, γ lactol, bis(tetrahydropyranyl)ether (formula XXlll: $R_4$ is THP and $Q_3$ is

and its 3β-hydroxy epimer.

A. Dimethyl 2-oxo-3,3-dimethylheptylphosphonate is made by adding 1.6M n-butyllithium in hexane (400 ml.) to a solution of dimethyl methylphosphonate (73.7 g.) and 1.3 l. of tetrahydrofuran at −66° C. To this mixture is then added a solution of ethyl 2,2-dimethylhexanoate (53 g.) in 150 ml. of tetrahydrofuran and the resulting mixture stirred at −70° C. for 2 hours. Then 46 ml. of acetic acid is added and the mixture is concentrated under reduced pressure. The residue is mixed with portions of dichloromethane (about 1.2 l.) and water (about 150 ml.) shaken and separated. The organic phase is dried over magnesium sulfate and concentrated. Distillation yields the title phosphonate.

B. A solution of the compound of part A above, 11 g., ) in 15 ml. of THF is added to a cold (5° C.) suspension of sodium hydride (55 percent, 2.26 g.) in 250 ml. of tetrahydrofuran with stirring. Thereafter the reaction mixture is stirred at about 25° C. for 2.5 hours and cooled to −10° C. To this mixture is added benzene solution of 3α-benzoloxy-2β-carboxy aldehyde-5α-hydroxy-1α-cyclopentaneacetic, γ lactone (Formula XVII: wherein $R_3$ is benzoyl, 150 gm.). After 1.5 hours 2 ml. of acetic acid is added and the tetrahydrofuran is distilled under vacuum. The residue is dissolved in ethyl acetate and the solution is washed with brine and dried over sodium sulfate and concentrated under reduced pressure. Chromatography over silica gel using 20-30 percent ethyl acetate in Skellysolve B for elution yields the corresponding optically active formula XVIII compound, 4.6 g., melting point 82°-83° C.

C. A solution of the product of part B above in 30 ml. of 1,2-dimethoxyethane is added to a mixture of zinc borohydride prepared from zinc chloride (7.95 g.) and sodium borohydride (1.75 g.) in 71 ml. of dry 1,2-dimethoxyethane. with stirring and cooling to −10° C. Stirring is continued for 2 hours at 0° C., and water (12 ml.) is cautiously added, followed by 25 ml. of ethyl acetate. The mixture is filtered and the filtrate is separated. The ethyl acetate solution is washed with brine, dried over sodium sulfate, and concentrated under reduced pressure to a mixture of the formula-XIX isomers. The alpha and beta isomers of the formula-XIX compound are separated by chromatography on silica gel, eluting with ethyl acetate to yield 1.2 g. of the alpha isomer and 0.4 g. of the beta isomer, respectively, of the optically active formula-XX compound.

D. Potassium carbonate (0.72 g.) is added to a solution of the optically active 3α-isomer of formula-XX compound prepared in paragraph C above (2.1 g.) in 35 ml. of methanol, and the mixture is stirred for 1 hour at about 25° C. Thereafter 75 ml. of chloroform is added, and the mixture is filtered, and the organic phase is concentrated under reduced pressure. The residue is taken up and dichloromethane and the solution is washed with brine. Concentration of the organic phase yields a residue which is triturated with Skellysolve B, then concentrated to the corresponding optically active formula XXI compound.

E. A solution of the optionally active formula XXI compound prepared in part D above (1.4 g.), 4.3 ml. of dihydropyran, and 0.023 g. of p-toluenesulfonic acid and 30 ml. of dichloromethane is stirred at about 25° C. for 30 min. The solution is washed with potassium bicarbonate solution, dried, and concentrated under reduced pressure to yield the corresponding optically active formula-XXII compound, 3.0 g.

F. Diisobutylaluminum hydride (2.5 ml.) in 16 ml. of toluene is added dropwise to a stirred solution of the optically active formula-XXII tetrahydropyranyl ether prepared in part E above (3.0 g.) in 25 ml. of toluene cooled to −70° C. Stirring is continued at −70° C. for 30 min. whereupon the solution of 9 ml. of tetrahydrofuran then 4.6 ml. of water is cautiously added. The mixture is filtered and the filtrate is washed with brine, dried, and concentrated to the pure 3-α-hydroxy isomer of the corresponding optically active formula XXIII title compound, 2.8 g.

Use of the 3β-isomer yields the corresponding 3β-product, following parts D, E, and F above.

Following the procedures of Preparation 1, the racemic formula XXIII lactol is prepared from the corresponding racemic starting material.

Preparation 2

(6-Carboxyhexyl) triphenylphosphonium bromide.

A mixture of 63.6 g. of 7-bromoheptanoic acid, 80 g. of triphenylphosphine, and 300 ml. of acetonitrile is refluxed for 68 hours. Then 200 ml. of acetonitrile is removed by distillation. After the remaining solution has cooled to room temperature, 300 ml. of benzene is added with stirring. After forming a crystal, the mixture is allowed to stand overnight. The solid which separates is collected by filtration giving 134.1 g. of the product as white prisms, melting point 185°-187° C. A portion is recrystallized from methanol-ether affording white prisms. melting point 185°-187° C. The infrared spectrum shows absorptions at 2850, 2570, 2480, 1710, 1585, 1485, 1235, 1200, 1185, 1160, 1115, 1000, 755, 725, and 695 cm.$^{-1}$ NMR peaks are observed at 1.2-1.9, 2.1-2.6, 3.3-4.0, and 7.7-8.0 δ.

Preparation 3 p-Benzamidophenol

A solution of p-hydroxyaniline (20 g.) in 200 ml. of pyridine is treated with benzoic anhydride (20 g.). After 4 hours at about 25° C., the mixture is concentrated under reduced pressure and the residue is taken up in 200 ml. of hot methanol and reprecipitated with 300 ml. of water. The product is recrystallized from hot acetonitrile as white crystals, 8.5 g., melting point 218°-218.5° C.

Preparation 4 p-(p-Acetamidobenzamide)phenol

A solution of p-acetamidobenzoic acid (12.5 g.) in 250 ml. of tetrahydrofuran is treated with triethylamine (11.1 ml.). The mixture is then treated with isobutylchloroformate (10.4 ml.) and, after 5 min. at about 25° C., with p-aminophenol (13.3 g.) in 80 ml. of dry pyridine. After 40 min. the crude product is obtained by addition of 2 liters of water. The product is recrystallized from 500 ml. of hot methanol by dilution with 300 ml. of water as white crystals, 5.9 g., melting point 275.0°-277.0° C.

Example 1

2a, 2b-Dihomo-16,16-dimethyl-PGF$_{2\alpha}$ (Formula XXVI: $R_1$ is hydrogen and $Q_2$ is

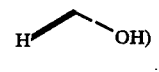

and its 15-epimer.

Refer to Chart A.

A. A stirred mixture of 6.3 g. of 57 percent sodium hydride in mineral oil (3.6 g.) and 150 ml. of dry dimethyl sulfoxide under nitrogen are heated at 55°-70° C. for 3.5 hours. The brown solution formed thereby is cooled to 20° C. in the cold water bath. Thereafter 35.4 g. of 6-carboxyhexyltriphenylphosphonium bromide (Preparation 2) is added in portions during 2 min. This solution is stirred for 1 hour at ambient temperature. Then a solution of 16.5 g. of 3α, 5α-dihydroxy-2β-(3α-hydroxy-4,4-dimethyltrans-1-octenyl)-cyclopentane acetaldehyde, γ lactol, bis (tetrahydropyranyl) ether, (Preparation 1) in 40 ml. of dry dimethylsulfoxide is added. The mixture is cooled to 25° C. The mixture is then stirred for 16 hours, 100 ml. of diethyl ether is then added and the mixture is cooled in an ice bath while a solution of 26.6 g. of potassium bisulfate in 150 ml. of water is slowly added. The mixture is diluted with 600 ml. of water and extracted with dichloromethane. The combined dichloromethane extracts are washed with water and dried with magnesium sulfate. Evaporation of the solvent under reduced pressure at 40° yields 45 g. of a yellow oil.

The oil is slurried with diethyl ether, and upon standing a solid separates. The mixture is then filtered. Diethyl ether solution is then extracted with cold aqueous 0.5 N sodium hydroxide solution and water. The combined aqueous extracts are cooled in an ice bath and covered with 150 ml. of diethyl ether. To this stirred mixture is added a cold solution of 22 g. of potassium bisulfate in 125 ml. of water. After the addition is complete, the layers are separated. The aqueous layer is extracted with 150 ml. of diethyl ether. The combined diethyl ether extracts are washed with 75 ml. of water and dried with magnesium sulfate. Evaporation of the solvent yields 11.3 g. of a yellow oil. This yellow oil is then chromatographed on 1.5 Kg. of acid washed silica gel. The column is eluted with 30 percent and 50 percent ethyl acetate in Skellysolve B. Fractions, as shown by silica gel thin layer chromatography to contain pure product, free from starting material, are combined yielding 7.31 g. of 2a, 2b-dihomo-16,16-dimethyl-PGF$_{2\alpha}$, 11,15-bis-tetrahydropyranyl ether.

B. A mixture of 1.6 g. of the reaction product of part A above, 10 ml. of tetrahydrofuran, 15 ml. of water and 30 ml. of acetic acid is heated at 40° C. for 4.5 hr. After addition of 50 ml. of water, the mixture is frozen in a dry ice acetone bath and then freeze dried until the mixture reaches room temperature. The oil so obtained is chromatographed on 200 g. of acid washed silica gel. The column is eluted with 60 percent ethyl acetate in Skellysolve B. Those fractions as shown by thin layer chromatography to contain the pure title compound are combined. Accordingly, 0.41 g. are obtained as a yellow oil. The mass spectrum shows absorptions at 374, 348, 320, 311, 293, 275, 257, 231, 129, and 121. Infrared absorption is observed at (cm.$^{-1}$) 3360, 2920, 2850, 2650, 1710, 1460, 1430, 1405, 1380, 1360, 1265, 1210, 1100, 1080, 1055, 1015, 995, and 970. NMR absorptions are observed at 0.7-1.1, 1.1-2.7, 3.7-4.4, 4.75-5.1, and 5.3-5.75 δ.

Following this procedure but using the 3β-hydroxy lactol the corresponding 15-epimer is obtained.

EXAMPLE 2

2a,2b-Dihomo-16,16-dimethyl-PGF$_{2\alpha}$, Methyl Ester (Formula XXVI: R$_1$ is methyl and Q$_2$ is

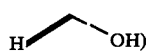

or its 15-epimer.

To a solution of 0.44 g. of 2a,2b-dihomo-16,16-dimethyl-PGF$_{2\alpha}$ (Example 1) in 100 ml. of diethyl ether is added an excess of ethereal diazomethane. The solution is allowed to stand at room temperature for 20 minutes. Then acetic acid (0.25 ml.) is added. Evaporation of the solvent under reduced pressure at 40° C. yields the yellow oil. The oil is chromatographed on 70 g. of TLC grade silica gel. The column is eluted with 50 percent acetone in dichloromethane. Fractions as shown by thin layer chromatography to contain pure product are combined. Accordingly, 0.13 g. of the title compound of this example are prepared as a colorless oil. Mass spectral peaks are observed at 405, 389, 388, 334, 325, 307, 289, 271, 257, 231, 219, 201, 145, 121, and 99. Infrared absorption is observed at (cm.$^{-1}$) 3370, 2930, 2850, 1735, 1460, 1435, 1360, 1260, 1200, 1170, 1100, 1080, 1055, 1015, 995, and 970. NMR absorption is observed 0.7-1.1, 1.1-2.9, 3.68, 3.7-4.4, and 5.3-5.7 δ.

Following the procedure of the above example but using the 15-epimer of Example 1, there are obtained the corresponding 15-epimeric product.

EXAMPLE 3

2a,2b-Dihomo-16,16-dimethyl-PGE$_2$ (Formula XXIX: R$_1$ is hydrogen and Q$_2$ is

or its 15-epimer.

A stirred solution of 5.68 g. of 2a,2b-dihomo-16,16-dimethyl-PGF$_{2\alpha}$, 11,15-bis tetrahydropyranyl ether (Example 1, part A) in 75 ml. of acetone is cooled in an ice methanol bath while 5 ml. of Jones reagent is added during 2 minutes. The mixture is then stirred at −20° C. for 45 minutes. Then 5 ml. of isopropanol is added, and the mixture is stirred at −20° C. for an additional 10 minutes. The mixture is then diluted with 500 ml. of water and extracted with dichloromethane. The combined extracts are washed with 50 ml. of water and dried with magnesium sulfate. Evaporation of the solvent under reduced pressure at 40° C. yields 5.69 g. of an oil. A mixture of the oil, 20 ml. of tetrahydrofuran, 45 ml. of water and 90 ml. of acetic acid are heated at 46° for 5 hours. After addition of 150 ml. of water the mixture is frozen in a dry-iceacetone bath and freeze dried until the mixture reaches room temperature. The oil obtained is chromatographed on a 500 g. column of acid washed silica gel. The column is eluted with 40 percent, 50 percent, 60 percent, and 80 percent ethyl acetate in Skellysolve B and 10 percent methanol in ethyl acetate. Those fractions as shown by silica gel thin layer chromatography to contain pure product are combined yielding 0.39 g. of the title compound as a pale yellow oil. Mass spectral peaks are observed 408, 390, 372, 315, 292, 274, 245, 218, 161, and 133. Infrared absorption is observed (cm.$^{-1}$) 3390, 2930, 2860, 2650, 1735, 1710, 1465, 1405, 1265, 1240, 1215, 1160, 1075, 995, and 975. NMR absorptions are observed at 0.8-1.1, 1.1-2.8, 3.7-4.3, and 5.2-5.8 δ.

Following the procedure of Example 3, but using in place of 15αstarting material, the 15-epimer, there is obtained the corresponding 15-epi title compound.

EXAMPLE 4

2a,2b-Dihomo-16,16-dimethyl-PGE$_2$, Methyl Ester (Formula XXIX: R$_1$ is methyl and Q$_2$ is

or its 15-epimer.

Following the procedure of Example 2, but using 2a,2b-dihomo-16,16-dimethyl-PGE$_2$ in place of the PGF$_2$α-type compound of Example 1, there is obtained the title compound of this Example as a yellow oil. Mass spectral peaks are observed at 404, 386, 373, 355, 323, 306, 305, 291, 288, 274, 273, 255, 245, 218, 161, 138, and 137. Infrared absorption is observed (cm.$^{-1}$) at 3430, 2930, 2860, 1745, 1460, 1440, 1365, 1260, 1205, 1165, 1080, 1020, 1000, and 975. NMR absorptions are observed at 0.7–1.1, 1.1–1.27, 3.68, 3.7–4.15, and 5.2–5.8 δ.

EXAMPLE 5

2a,2b-Dihomo-16,16-dimethyl-PGF$_{1\alpha}$, (Formula XXVII: R$_1$ is hydrogen and Q$_2$ is

and its methyl ester.

A. A mixture of 0.50 g. of 2a,2b-dihomo-16,16-dimethyl-PGF$_{2\alpha}$, and 100 mg. of 5 percent palladium on carbon in 150 ml. of ethyl acetate is stirred at −15° C. (methanolice) under one atmosphere of hydrogen. Progress of the reaction is monitored by TLC (ethyl acetate) of aliquots using silver nitrate silica gel. After 95 min., the reaction is complete. The mixture is filtered through Celite, washing well with ethyl acetate. Rotary evaporation of the filtrate gives an oil which readily crystallized at room temperature. Recrystallization once from hexane-ethyl acetate yields the compound of this example.

The mass spectrum for the trimethylsilyl derivative shows base peak absorption at 685.4546 and other peaks at 700, 601, 511, 485, and 217. NMR absorptions for deuterochloroform solutions are observed at 0.8–1.1, 1.1–2.6, 3.7–4.35, and 5.42–5.74 δ. Infrared absorptions are observed at 3370, 2960, 2920, 2850, 2660, 1710, 1465, 1410, 1385, 1365, 1260, 1200, 1110, 1080, 1050, 1020, 995, 970, and 725 cm.$^{-1}$.

B. The methyl ester of the free acid, prepared in part A, above is prepared by reaction with diazomethane following the procedure described above.

The mass spectrum for the trimethylsilyl derivative shows base peak absorption at 627.4283 and other peaks at 642, 611, 543, 521, 453, 427, 243, and 217. NMR absorptions for deuterochloroform solutions are observed at 0.7–1.1, 1.1–2.6, 3.68, 3.7–4.22, and 5.4–5.68 δ. Infrared absorptions are observed at 3380, 2920, 2860, 1740, 1670, 1470, 1435, 1380, 1365, 1260, 1200, 1175, 1110, 1080, 1050, 1020, 995, and 970 cm.$^{-1}$.

EXAMPLE 6

2a,2b-Dihomo-16,16-dimethyl-PGF$_{2\beta}$, Methyl Ester (Formula XXXIII: R$_1$ is methyl, Q$_2$ is

and X is cis—CH=CH—).

A. 2a,2b-Dihomo-16,16-dimethyl-PGE$_2$, methyl ester is reacted with sodium borohydride in methanol at −15° C. to produce mixed 9-hydroxy epimers.

B. The title compound of this example is separated from its 9-alpha epimer by column chromatography on silica gel using the epimeric mixture of part A of this example.

The mass spectrum for the trimethylsilyl derivative shows base peak absorption at 625.4121 and other peaks at 640, 609, 541, 451, 425, 361, 335, 243, and 217. NMR absorptions for deuterochloroform solutions are observed at 0.7–1.1, 1.1–2.5, 2.6–3.1, 3.65, 3.75–4.3, and 5.3–5.66 δ. Infrared absorptions are observed at 3360, 3000, 2960, 2920, 2860, 1740, 1720, 1460, 1435, 1365, 1265, 1210, 1170, 1095, 1040, 1020, 1000, and 970 cm.$^{-1}$.

EXAMPLE 7

2a,2b-Dihomo-16,16-dimethyl-PGE$_1$ (Formula XXX: R$_1$ is hydrogen and Q$_2$ is

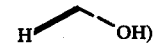

and its methyl ester.

A. Following the procedure described in Example 5, but using in place of the PGF$_{2\alpha}$-type starting material the PGE$_2$-type compound of Example 3, there is prepared the title compound of this example.

The mass spectrum for the trimethylsilyl derivative shows base peak absorption 611.3953 and other peaks 626, 527, 521, 437, 383, and 243. NMR absorptions for deutrochloroform solutions are observed at 0.8–1.1, 1.1–2.7, 3.7–4.2, 5.15–5.45, and 5.5–5.8 δ. Infrared absorptions are observed at 3400, 2920, 2850, 2660, 1740, 1710, 1585, 1465, 1410, 1385, 1365, 1280, 1245, 1210, 1160, 1100, 1075, 1015, 995, 970, and 725 cm.$^{-1}$.

B. The free acid above is transformed to the corresponding methyl ester by reaction with diazomethane as described above.

The mass spectrum for the trimethylsilyl derivative shows base peak absorption 553.3744 and other peaks at 568, 537, 469, 379, 325, and 243. NMR absorptions of deuterochloroform solutions are observed at 0.75–1.1, 1.1–3.0, 3.65, 3.7–4.16, and 5.5–5.79 δ. Infrared absorptions are observed at 3420, 2930, 2860, 1745, 1465, 1440, 1365, 1250, 1200, 1165, 1105, 1080, 1020, 1000, and 975 cm.$^{-1}$.

EXAMPLE 8

2a,2b-Dihomo-16,16-dimethyl-PGF$_{1\beta}$, Methyl Ester (Formula XXXIII: R$_1$ is methyl, Q$_2$ is

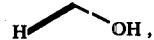

and X is cis—CH=CH—).

The compound of this example is prepared by reduction of the methyl ester compound of Example 7 according to the procedure described in Example 5.

The mass spectrum for the trimethylsilyl derivative shows base peak absorption at 627.4289 and other peaks at 642, 611, 543, 521, 453, 427, 243, and 217. NMR absorptions for deuterochloroform solutions are observed at 0.8–1.1, 1.1–2.5, 3.68, 3.8–4.2, and 5.45–5.68 δ. Infrared absorptions are observed 3260, 3170, 1740, 1670, 1440, 1390, 1350, 1325, 1250, 1200, 1175, 1080, 1035, and 975 cm.$^{-1}$.

EXAMPLE 9

2a,2b-Dihomo-16,16-dimethyl-PGF$_{2\alpha}$ sodium salt.

A solution of 2a,2b-dihomo-16,16-dimethyl-PGF$_{2\alpha}$ (Example 1, 100 mg.) in 50 ml. of water ethanol mixture (1:1) is cooled to 5° C. and neutralized with equivalent amount of 0.1 N aqueous sodium hydroxide solution. The neutral solution is concentrated to a residue of the title compound.

Following the procedure of Example 9, but using potassium hydroxide, calcium hydroxide, tetramethyl ammonium hydroxide, or benzyl trimethyl ammonium hydroxide in place of sodium hydroxide, there are obtained the corresponding salts of 2a,2b-dihomo-16,16-dimethyl-PGF$_{2\alpha}$. Likewise following the procedure of Example 9, each of these 2a,2b-dihomo-16,16-dimethyl-PGE-type or PGF-type acids, or their 15-epimers, is transformed to the sodium, potassium, calcium, tetramethyl ammonium, or benzyl trimethyl ammonium salt.

EXAMPLE 10 p-Acetamidophenyl Ester of 2a,2b-Dihomo-16,16-dimethyl-PGF$_{2\alpha}$.

A solution of 2a,2b-dihomo-16,16-dimethyl-PGF 2α- (compound of Example 1) in acetone is treated at −10° C. with twice the stoichiometric amount of triethylamine as prostaglandin analog and also with an equal quantity of isobutylchloroformate, whereupon triethylamine hydrochloride is precipitated. After 5 minutes the mixture is treated with several fold stoichiometric excess (over the prostaglandin analog) of p-acetamidophenol in pyridine for 3 hours at 25° C. The solvent is removed under reduced pressure and the residue is taken up in acetonitrile and again concentrated. The crude residue is subjected to silica gel chromatography, eluting with ethyl acetate and methanol (ratio 90:10). The residue obtained by concentration of selected fractions, a solid on chilling, is the compound of this example.

Following the procedure of Example 10 using each of the PGF- and PGE-type free acids of examples above and a phenol or naphthol selected from the group consisting of p-acetamidophenol, p-(p-acetamidobenzamido) phenol, p-benzamidophenol, p-hydroxyphenylurea, p-hyroxybenzaldehyde semicarbazone, and 2-naphthol, the corresponding substituted phenyl or naphthyl esters is obtained.

I claim:

1. An optically active compound of the formula:

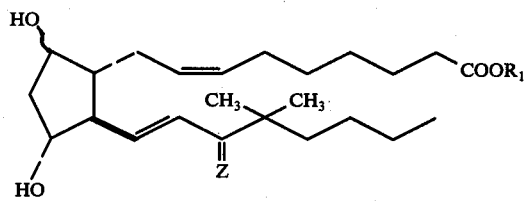

wherein Z is

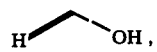

or

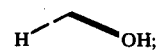

and wherein R$_1$ is hydrogen, alkyl of one to 12 carbon atoms, inclusive,

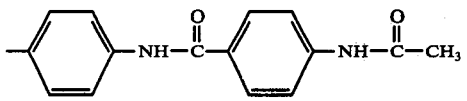

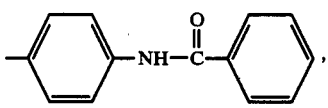

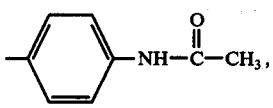

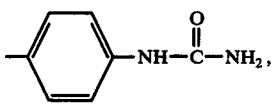

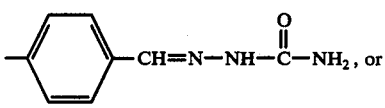

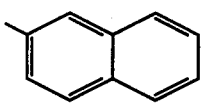

or pharmacologically acceptable salts thereof when R$_1$ is hydrogen.

2. A compound according to claim 1, wherein Z is

3. 2a,2b-Dihomo-16,16-dimethyl-PGF$_{2\alpha}$, a compound according to claim 2, wherein R$_1$ is hydrogen.

4. 2a,2b-Dihomo-16,16-dimethyl-PGF$_{2\alpha}$, methyl ester, a compound according to claim 2, wherein R$_1$ is methyl.

5. A compound according to claim 1, wherein Z is

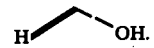

6. 2a,2b-Dihomo-15-epi-16,16-dimethyl-PGF$_{2\alpha}$, a compound according to claim 5, wherein R$_1$ is hydrogen.

7. 2a,2b-Dihomo-15-epi-16,16-dimethyl-PGF$_{2\alpha}$, methyl ester, a compound according to claim 5, wherein R$_1$ is methyl.

* * * * *

UNITED STATES PATENT OFFICE
CERTIFICATE OF CORRECTION

Patent No. 4,067,891           Dated   10 January 1978

Inventor(s)   Gilbert A. Youngdale

It is certified that error appears in the above-identified patent and that said Letters Patent are hereby corrected as shown below:
Column 9, lines 38-45, that portion of the formula reading

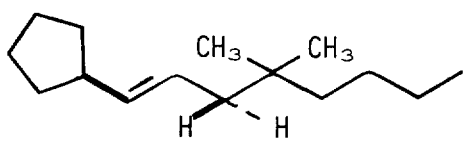     should read     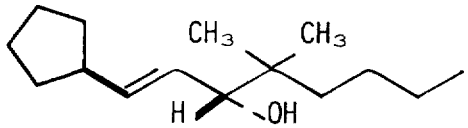

Column 10, lines 20-29, that portion of the formula reading
                                         should read

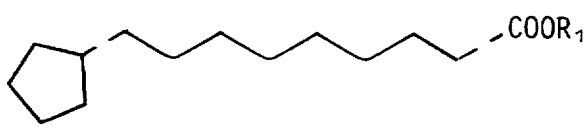     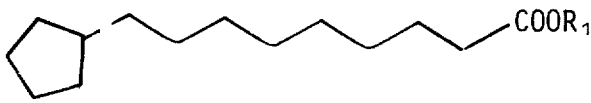

Column 22, line 54, "and chloraform The" should read -- and chloroform. The --;

Column 32, lines 50-54, " H⁀OH " should read -- H⁀OH --.

Signed and Sealed this

Twenty-ninth Day of September 1981

[SEAL]

*Attest:*

*Attesting Officer*

GERALD J. MOSSINGHOFF
*Commissioner of Patents and Trademarks*